(12) United States Patent
Takahashi et al.

(10) Patent No.: US 7,891,456 B2
(45) Date of Patent: Feb. 22, 2011

(54) ANTI-DRUNK DRIVING APPARATUS FOR VEHICLE

(75) Inventors: Akio Takahashi, Shioya-gun (JP); Shinsuke Ueda, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 213 days.

(21) Appl. No.: 12/241,698

(22) Filed: Sep. 30, 2008

(65) Prior Publication Data

US 2009/0090577 A1   Apr. 9, 2009

(30) Foreign Application Priority Data

Oct. 3, 2007   (JP) .............................. 2007-259836

(51) Int. Cl.
*B60K 28/06* (2006.01)
(52) U.S. Cl. ....................... 180/272; 340/576
(58) Field of Classification Search ................. 180/272; 340/576

See application file for complete search history.

(56) References Cited

U.S. PATENT DOCUMENTS

| | | | |
|---|---|---|---|
| 7,451,852 B2 * | 11/2008 | Stewart et al. | 180/272 |
| 2003/0117287 A1 * | 6/2003 | Crespo | 340/576 |
| 2006/0097881 A1 * | 5/2006 | Crespo | 340/573.1 |
| 2007/0144812 A1 * | 6/2007 | Stewart et al. | 180/272 |
| 2008/0117063 A1 * | 5/2008 | Crespo | 340/576 |
| 2009/0043409 A1 * | 2/2009 | Ota | 700/90 |
| 2010/0108425 A1 * | 5/2010 | Crespo et al. | 180/272 |

FOREIGN PATENT DOCUMENTS

| | | |
|---|---|---|
| JP | 7-9924 | 1/1995 |
| JP | 2004-249847 | 9/2004 |
| JP | 2005-1572 | 1/2005 |
| JP | 2005-118177 | 5/2005 |
| JP | 2005-184184 | 7/2005 |
| JP | 2007-24543 | 2/2007 |
| JP | 2007-107377 | 4/2007 |
| JP | 2007-186144 | 7/2007 |
| JP | 2007-524441 | 8/2007 |

OTHER PUBLICATIONS

Japanese Office Action for Application No. 2007-259836, dated May 7, 2007.

* cited by examiner

*Primary Examiner*—Paul N Dickson
*Assistant Examiner*—Drew Brown
(74) *Attorney, Agent, or Firm*—Nelson Mullins Riley & Scarborough LLP; Anthony A. Laurentano, Esq.

(57) ABSTRACT

An anti-drunk driving apparatus for a vehicle including: an alcohol drinking determination device which determines whether or not a first person seated in a driver's seat is drunk; a driving restriction device which restricts driving of the vehicle in a case where it is determined that the first person seated in the driver's seat is drunk by the alcohol drinking determination device; a driving intention presumption device which presumes whether or not a second person seated in the driver's seat has an intention to drive; a photograph device which photographs the faces of the first and second persons; and a person identification device which determines whether or not the first and second persons are the same by comparing their faces in images, wherein if it is determined that the first and the second persons are not the same, the driving restriction device restricts driving of the vehicle.

2 Claims, 3 Drawing Sheets

FIG. 3

| ALCOHOL CONCENTRATION | FACE IMAGE IN ALCOHOL CONCENTRATION MEASUREMENT | FACE IMAGE WHEN SHIFT POSITION IS CAHNGED | DEPARTURE OF VEHICLE |
|---|---|---|---|
| LESS THAN THRESHOLD VALUE | 31 | 32A (32) IDENTICAL | ○ |
|  |  | 32B (32) DIFFERENT | × |
| EQUAL TO OR MORE THAN THRESHOLD VALUE | | | × |

ANTI-DRUNK DRIVING APPARATUS FOR VEHICLE

Priority is claimed on Japanese Patent Application No. 2007-259836, filed Oct. 3, 2007, the content of which is incorporated herein by reference.

BACKGROUND OF THE INVENTION

1. Field of the Invention

The present invention relates to an anti-drunk driving apparatus for a vehicle.

2. Description of the Related Art

In recent years, vehicles with measures being taken to eliminate drunk driving have been proposed (see, for example, Japanese Unexamined Patent Application, First Publication No. 2004-249847).

In the hazard prevention method or apparatus disclosed in the above prior patent document, it is determined whether a driver is drunk or not by comparing a detected signal value with an alcohol sensor at a driver's seat and a detected signal value with an alcohol sensor at a passenger's seat. If it is determined the driver is drunk, the vehicle cannot be started or driven.

However, in the above apparatus or in other anti-drunk driving apparatuses which have been proposed to date, even a driver under the influence can start and drive the vehicle if an alcohol concentration measurement is performed to the other person instead of the driver. In other words, impersonation is possible in those apparatuses.

In view of the above-described circumstances, the present invention has an object of providing an anti-drunk driving apparatus for a vehicle, which only enables a person who is not drunk to drive.

SUMMARY OF THE INVENTION

In order to achieve the above-described object, the present invention employs the following. Namely, the present invention employs an anti-drunk driving apparatus for a vehicle including: an alcohol drinking determination device which determines whether or not a first person seated in a driver's seat is drunk; a driving restriction device which restricts driving of the vehicle in a case where it is determined that the first person seated in the driver's seat is drunk by the alcohol drinking determination device; a driving intention presumption device which presumes whether or not a second person seated in the driver's seat has an intention to drive; a photograph device which photographs the face of the first person seated in the driver's seat, and the face of the second person seated in the driver's seat; and a person identification device which compares an image of the face of the first person seated in the driver's seat and an image of the face of the second person seated in the driver's seat, and thereby determines whether or not the first person seated in the driver's seat and the second person seated in the driver's seat are the same, wherein if it is determined by the person identification device that the first person seated in the driver's seat and the second person seated in the driver's seat are not the same, the driving restriction device restricts driving of the vehicle.

According to the above-described anti-drunk driving apparatus, whether or not the person seated in the driver's seat during the alcohol drinking determination and the person seated in the driver's seat during the driving intention presumption are identical can be determined by the person identification device. For this reason, impersonation in the alcohol drinking determination can be prevented. As a result, the anti-drunk driving apparatus enables only a person who is not drunk to drive.

It may be arranged such that the driving intention presumption device presumes that the second person seated in the driver's seat has an intention to drive when the transmission of the vehicle is not in a park position or in a neutral position.

In this case, by presuming the person seated in the driver's seat having an intention to drive when the transmission is not in a parking or neutral position, the driving intention of the person seated in the driver's seat can reliably be recognized.

It may be arranged such that the anti-drunk driving apparatus for a vehicle further includes a vehicle speed sensor which measures the speed of the vehicle, wherein the driving intention presumption device presumes that the second person seated in the driver's seat has an intention to drive when the speed of the vehicle measured by the vehicle speed sensor is equal to or more than a predetermined value.

In this case, by presuming the person seated in the driver's seat having an intention to drive when the speed of the vehicle measured by the vehicle speed sensor is equal to or more than a predetermined value, the driving intention of the person seated in the driver's seat can reliably be recognized.

BRIEF DESCRIPTION OF THE DRAWINGS

FIG. 3 is a summary table of conditions where a vehicle is allowed to start moving in the anti-drunk driving apparatus for a vehicle according to the embodiment of the present invention.

DETAILED DESCRIPTION OF THE INVENTION

An embodiment of the present invention is explained below with reference to FIGS. 1 through 3.

(Anti-Drunk Driving Apparatus for a Vehicle)

Figure 1:
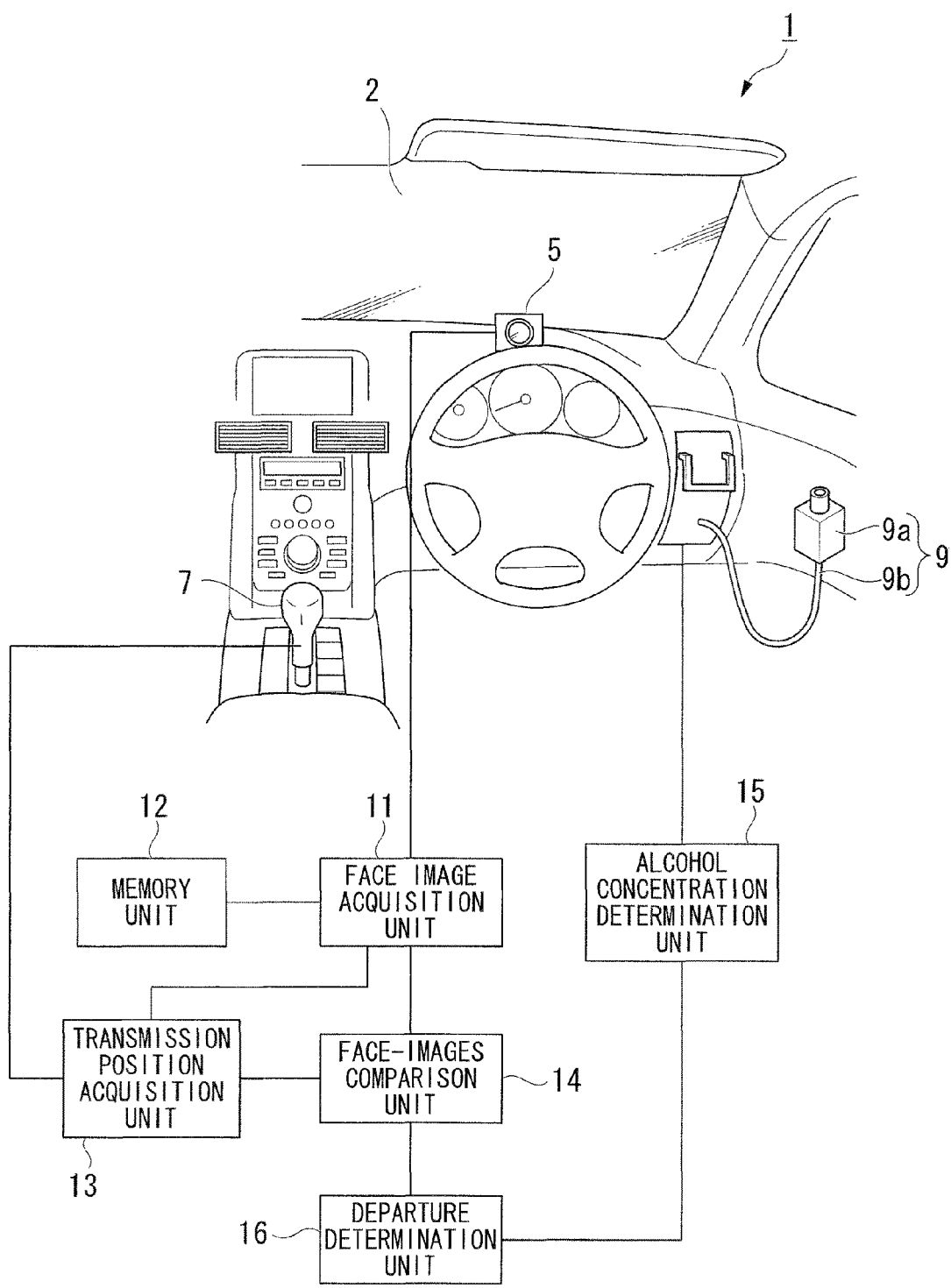
FIG. 1 is a schematic structural view showing an anti-drunk driving apparatus for a vehicle according to an embodiment of the present invention.

FIG. 1 is a schematic structural view showing an anti-drunk driving apparatus for a vehicle according to the present embodiment.

The anti-drunk driving apparatus 1 for a vehicle includes a camera (photograph device) 5 which photographs within a predetermined range the face of a person seated in the driver's seat of the present vehicle 2, a face image acquisition unit 11 which acquires face images photographed by the camera 5, a memory unit 12 which temporarily stores data of the face images photographed by the camera 5, a transmission position acquisition unit 13 which acquires information on a lever position of the transmission of the present vehicle 2, a face-images comparison unit 14 which determines whether or not persons in the face images are identical by comparing data of those face images (e.g. two face images), an alcohol concentration determination unit 15 which measures the alcohol concentration of breath blown to a alcohol sensor 9 that is provided to the present vehicle 2, and a departure determination unit 16 which allows the present vehicle 2 to start moving based on the result obtained in the face-images comparison unit 14 and the alcohol concentration determination unit 15.

The camera 5 is disposed, for example, on a dashboard portion in front of a steering wheel which faces the driver's seat, so as to photograph the face of a person seated in the driver's seat of the present vehicle 2. The camera 5 is, for example, a visible camera such as a CCD camera. Images photographed by the camera 5 are input to the face image acquisition unit 11 in a computer which is mounted on the present vehicle 2. In addition, after a key is put into a lock of the present vehicle 2, for example, the camera 5 is capable of photographing the face of a person seated in the driver's seat (refer to a first face image 31 in FIG. 3) and measuring an alcohol concentration at substantially the same time.

The face image acquisition unit 11 performs a predetermined image processing such as filtering and binarization for the image photographed by the camera 5, and thereby generates image data consisting of two dimensional array pixels. The face image data obtained in the face image acquisition unit 11 is temporarily stored at the memory unit 12.

The transmission position acquisition unit 13 detects where the shift lever of the transmission 7 of the present vehicle 2 is positioned and acquires the information. It is determined in the transmission position acquisition unit 13 whether or not the shift lever of the transmission 7 is in the parking or the neutral position, or the other position such as drive position. If the transmission position acquisition unit 13 detected that the shift lever of the transmission 7 is in the drive position or the other positions in which the vehicle starts to move, a signal is transmitted to the face image acquisition unit 11. With the signal transmission, the camera 5 is activated to acquire a face image of a person seated in the driver's seat (refer to a second face image 32 in FIG. 3).

The face-images comparison unit 14 determines whether or not those persons are identical by comparing the first face image 31 and the second face image 32 which are photographed by the camera 5. The comparison of the two face images for the identification determination is made, for example, by extracting the eyes and nose from each of the face images as characteristic points, and then measuring those sizes, the distance between the eyes, the distance between the eye and the nose, and so on.

The alcohol sensor 9 is for determining whether or not a person seated in the driver's seat is drunk or not based on his breath and is disposed, for example, on a dash board portion which is to the right of the steering wheel. A main body portion 9a of the alcohol sensor 9 is connected to a tip of a cable 9b which is fixed to a dash board portion. In addition, the main body portion 9a can be moved to the vicinity of a head of a person seated in the driver's seat. Information with regard to breath blown to the alcohol sensor 9 is input to the 15 in the computer which is mounted on the present vehicle 2.

The departure determination unit 16 receives information on whether or not those persons in the first face image 31 and the second face image 32 are identical from the face-images comparison unit 14. In addition, the departure determination unit 16 receives information on the alcohol concentration of the breath blown to the alcohol sensor 9 from the alcohol concentration determination unit 15. Only if the persons in the two face images are identical and the alcohol concentration is high enough to be detrimental to driving, the departure determination unit 16 allows the present vehicle 2 to start moving, while the departure determination unit 16 restricts the present vehicle 2 from starting to move in the other conditions.

Note that, restricting the present vehicle 2 is achieved by stopping the engine, forcibly positioning the shift lever of the transmission 7 to neutral, or the like.

(Prevention of Drunk Driving)

Next, a method of preventing drunk driving using the anti-drunk driving apparatus 1 for a vehicle will be explained.

Figure 2:
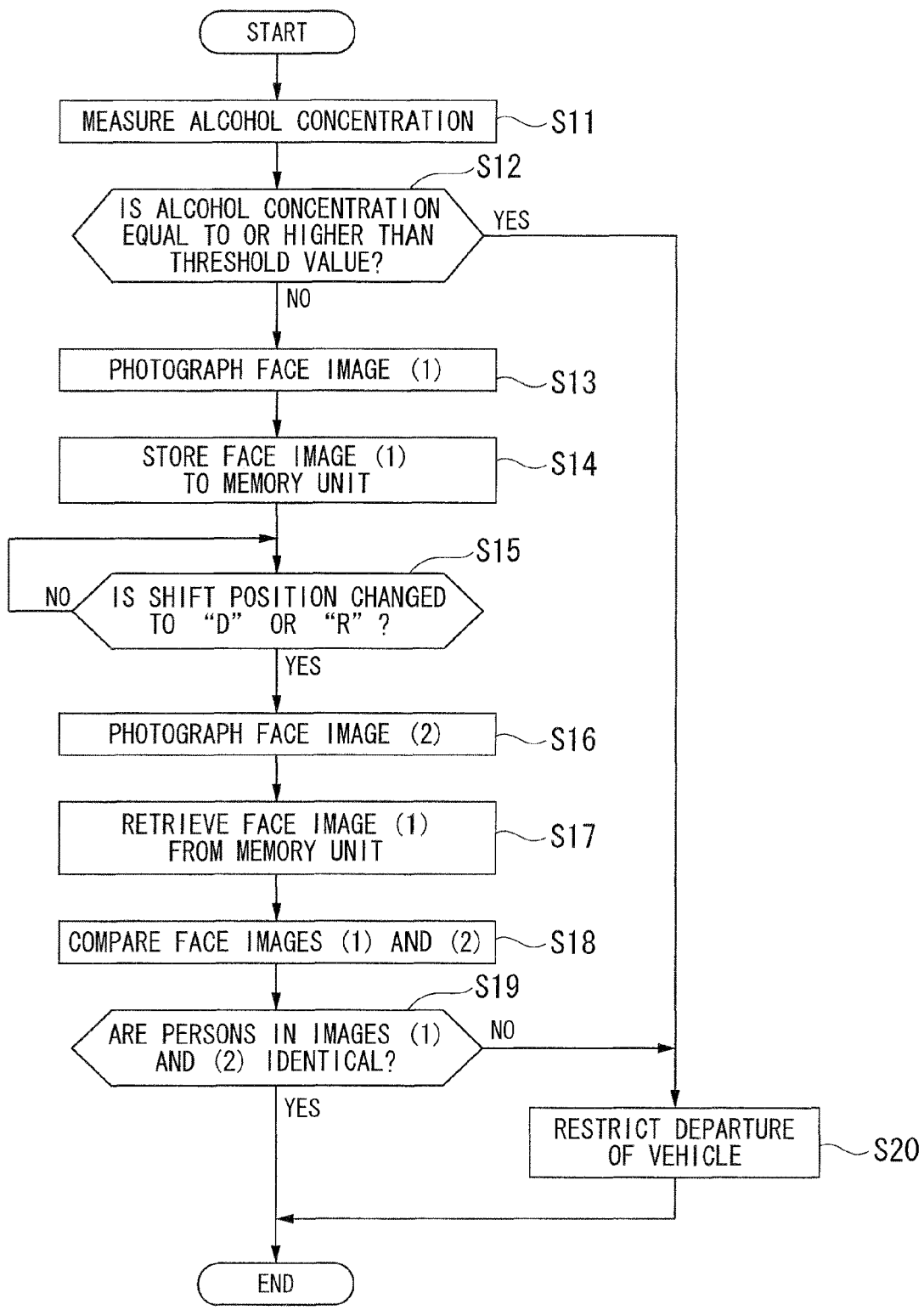
FIG. 2 is a flow chart showing a method of preventing drunk driving using the anti-drunk driving apparatus for a vehicle according to the embodiment of the present invention.

FIG. 2 is a flow chart showing the method of preventing drunk driving using the anti-drunk driving apparatus 1 for a vehicle according to the present embodiment.

In S11, as shown in FIG. 2, by inserting a key into a lock of the present vehicle 2, the alcohol sensor 9 is activated. When a person seated in the driver's seat blows his breath into the alcohol sensor 9, an alcohol concentration measurement is performed. Then the process proceeds to S12.

In S12, the alcohol concentration determination unit 15 determines whether or not the alcohol concentration of the breath blown into the alcohol sensor 9 in S11 is equal to or higher than a threshold value. That is, the alcohol concentration determination unit 15 determines whether or not the person is drunk or not. If the alcohol concentration is equal to or higher than the threshold value, then the process proceeds to S20, otherwise the process proceeds to S13.

In S13, the camera 5 is activated to photograph the face of the person seated in the driver's seat (the first face image 31), and then the process proceeds to S14.

In S14, data of the first face image 31 photographed in S13 is input to the face image acquisition unit 11 where a predetermined image processing is performed to the data. The processed data of the face image is then temporarily stored to the memory unit 12, and then the process proceeds to S15.

In S15, the shift position of the transmission of the present vehicle 2 is detected with the transmission position acquisition unit 13. If the shift position is in D (Drive) or R (Reverse), then the process proceeds to S16. That is, if the shift position is moved to start moving the present vehicle 2 to either direction, then the process proceeds to the next step, otherwise stays in the loop of S15.

In S16, at substantially the same time as the shift position is moved to D or R, the face of a person seated in the driver's seat is photographed by the camera 5 (the second face image 32), and then the process proceeds to S17.

In S17, the data of the first face image temporarily stored in the memory unit 12 is retrieved, and then the process proceeds to S18.

In S18, the first face image 31 and the second face image 32 are compared in the face-images comparison unit 14, and the process proceeds to S19.

In S19, it is determined whether or not those persons in the first face image 31 and in the second face image 32, which are compared in S18, are identical in the face-images comparison unit 14. If it is determined that the persons are not identical, then the process proceeds to S20, otherwise the process is terminated to allow the present vehicle 2 to start moving.

In S20, departure of the present vehicle 2 is immediately restricted in accordance with a determination in S12 that the alcohol concentration is equal to or higher than the threshold value, which is considered to signify drunk driving. In addition, departure of the present vehicle 2 is restricted if it is determined that the persons in the first face image 31 and the second face image 32 are not identical in S19, which is considered to show that a person seated in the driver's seat is attempting to drive by impersonating another person such as a fellow passenger who was the a subject of the alcohol concentration measurement. Then the process is terminated.

FIG. 3 is a summary table of conditions where the vehicle is allowed to start moving.

As shown in FIG. 3, departure of the present vehicle 2 is restricted without identifying face images if the alcohol concentration is equal to or higher than the threshold value. In the case where the alcohol concentration is less than the threshold value, then the first face image 31 and the second face image 32 are compared. Only if the person in the second face image 32 is identical to the person in the first face image 31 (in the case of the second face image 32A), the present vehicle 2 is allowed to start moving. In contrast, the person in the second face image 32 is different from the person in the first face image 31 (in the case of the second face image 32B), the present vehicle 2 is not allowed to start moving. In this configuration, the number of photographs taken by the camera 5 in the alcohol drinking determination is minimized. Thereby, the alcohol drinking determination is efficiently performed.

As is described above, the anti-drunk driving apparatus 1 according to the present embodiment includes: the alcohol concentration determination unit 15 which determines whether or not a person seated in the driver's seat is drunk; the departure determination unit 16 which restricts driving of the present vehicle 2 in a case where it is determined that the person is drunk by the alcohol concentration determination unit 15; the transmission position acquisition unit 13 which presumes whether or not a person seated in the driver's seat has an intention to drive; the camera 5 which photographs the face of a person seated in the driver's seat; and the face-images comparison unit 14 which compares an image of the face of the person (the first face image 31) being tested by the alcohol concentration determination unit 15 using the alcohol sensor 9 and an image of the face of the person (the second face image 32) who is determined to have an intention to drive by the transmission position acquisition unit 13, and thereby determines whether or not those persons are the same, wherein the departure determination unit 16 restricts driving of the present vehicle 2 if it is determined that the persons are not the same by the face-images comparison unit 14.

According to the above-described anti-drunk driving apparatus 1, since it can be determined by the face-images comparison unit 14 (person identification device) whether or not the person seated in the driver's seat (the person who blows his breath to the alcohol sensor 9) during alcohol drinking determination (during the alcohol concentration measurement) and the person seated in the driver's seat when the transmission position acquisition unit 13 detects that the shift position is moved D or R (during the driving intention presumption) are identical, impersonation in the alcohol drinking determination can be prevented. As a result, the anti-drunk driving apparatus enables only a person who is not drunk to drive.

In addition, since a person in the driver's seat is presumed to have an intention to drive when the position of the transmission 7 is switched to the other position other than the park or neutral, the driving intention of the driver can reliably be recognized.

Note that the technical scope of the present invention is not limited to the above-described embodiment, but includes various kinds of modifications that can be added to the above-described embodiment without departing from the spirit or scope of the present invention. Specifically, the concrete structures or the values described in the above embodiment merely shows one example among many and can be arbitrarily modified.

For example, since it is presumed that a person seated in the driver's seat has an intention to drive based on the position of the shift lever of the transmission in the above-described embodiment, a vehicle speed meter may be employed to presume the driving intention, in which it is determined that the person has an intention to drive when the vehicle speed measured by the vehicle speed meter is equal to or higher than the predetermined value. Furthermore, it may be determined that the person has an intention to drive when the person puts his foot down on the accelerator or release his foot off the brake pedal.

In addition, since stopping the engine or forcibly positioning the shift to neutral as a method of restricting the vehicle from starting to move is illustrated in the above-described embodiment, another method may be employed. For example, forcibly applying the brake which cannot be released or locking the handle may be employed for the purpose of restricting the vehicle from starting to move.

While a preferred embodiment of the invention has been described and illustrated above, it should be understood that this is exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An anti-drunk driving apparatus for a vehicle comprising:
   an alcohol drinking determination device which determines whether or not a first person seated in a driver's seat is drunk;
   a driving restriction device which restricts driving of the vehicle in a case where it is determined that the first person seated in the driver's seat is drunk by the alcohol drinking determination device;
   a driving intention presumption device which presumes whether or not a second person seated in the driver's seat has an intention to drive;
   a photograph device which photographs the face of the first person seated in the driver's seat, and the face of the second person seated in the driver's seat; and
   a person identification device which compares an image of the face of the first person seated in the driver's seat and an image of the face of the second person seated in the driver's seat, and thereby determines whether or not the first person seated in the driver's seat and the second person seated in the driver's seat are the same, wherein
      if it is determined by the person identification device that the first person seated in the driver's seat and the second person seated in the driver's seat are not the same, the driving restriction device restricts driving of the vehicle,
   wherein the driving intention presumption device presumes that the second person seated in the driver's seat has an intention to drive when the transmission of the vehicle is not in a park position or in a neutral position.

2. An anti-drunk driving apparatus for a vehicle comprising:
   an alcohol drinking determination device which determines whether or not a first person seated in a driver's seat is drunk;
   a driving restriction device which restricts driving of the vehicle in a case where it is determined that the first person seated in the driver's seat is drunk by the alcohol drinking determination device;
   a driving intention presumption device which presumes whether or not a second person seated in the driver's seat has an intention to drive;
   a photograph device which photographs the face of the first person seated in the driver's seat, and the face of the second person seated in the driver's seat; and
   a person identification device which compares an image of the face of the first person seated in the driver's seat and an image of the face of the second person seated in the driver's seat, and thereby determines whether or not the first person seated in the driver's seat and the second person seated in the driver's seat are the same, wherein if it is determined by the person identification device that the first person seated in the driver's seat and the second person seated in the driver's seat are not the same, the driving restriction device restricts driving of the vehicle, the anti-drunk driving apparatus further comprising a vehicle speed sensor which measures the speed of the vehicle, wherein the driving intention presumption device presumes that the second person seated in the driver's seat has an intention to drive when the speed of the vehicle measured by the vehicle speed sensor is equal to or more than a predetermined value.

* * * * *